United States Patent [19]

Hansen

[11] 3,987,673
[45] Oct. 26, 1976

[54] ULTRASONIC TRANSDUCER DEVICES
[75] Inventor: Per Loubaerg Hansen, Gentofte, Denmark
[73] Assignee: National Research Development Corporation, London, England
[22] Filed: Jan. 3, 1975
[21] Appl. No.: 538,325

[30] Foreign Application Priority Data
Jan. 3, 1974 United Kingdom................... 313/74

[52] U.S. Cl............................ 73/194 A; 128/2.05 F
[51] Int. Cl.² ...................... G01F 1/66; A61B 5/02
[58] Field of Search ............. 73/194 A; 128/2.05 F, 128/2.05 Z

[56] References Cited
UNITED STATES PATENTS

| | | | |
|---|---|---|---|
| 3,498,290 | 3/1970 | Shaw et al. .................. | 73/194 A X |
| 3,710,792 | 1/1973 | Light............................ | 73/194 A X |
| 3,712,119 | 1/1973 | Cross et al........................... | 73/67.7 |
| 3,766,517 | 10/1973 | Fahrbach...................... | 73/194 A X |
| 3,889,533 | 6/1975 | Balser........................... | 73/194 A X |

Primary Examiner—Charles A. Ruehl
Attorney, Agent, or Firm—Cushman, Darby & Cushman

[57] ABSTRACT

A flowmeter for measuring blood flow in a vascular channel by Doppler Techniques has an assembly of electro-ultrasonic transducers which direct ultrasonic radiation to a zone spaced from the assembly and receive radiation reflected therefrom. The transducers are spaced apart and capable of providing two radiation beam paths from transmitting to receiving transducers after reflection from the zone. The transducers are directed such that part of one of the beam paths forms an acute angle with the direction of blood flow and part of the other beam path forms an obtuse angle with the direction of blood flow. The reflected signals are shifted in frequency by Doppler effect and their instantaneous difference frequency is monitored and expressed directly in terms of velocity.

17 Claims, 16 Drawing Figures

ULTRASONIC TRANSDUCER DEVICES

BACKGROUND OF THE INVENTION

This invention relates to flowmeters and more particularly, but not exclusively, to flowmeters for the provision of blood velocity measurements by use of non-invasive ultrasonic Doppler techniques.

A difficulty in obtaining reproducible measurements with such techniques is that the factor of proportionality between observed Doppler shifts and velocity involves the cosine of the angle between the direction of the ultrasonic beam and the direction of flow and accurate knowledge of this angle is required except when it is possible to aim the beam so that the relevant angle is close to zero. Since the great majority of the more readily accessible blood vessels such as the limb arteries and the carotids run more or less parallel to the body surface, it is not possible to render the beam/vessel angle close to zero and it is therefore necessary to establish this angle with some accuracy if absolute velocity measurements are required, or to ensure that the angle remains constant if indications of velocity changes are desired by serial observations. In either of these last situations practical difficulty arises. The present invention has been arrived at from a consideration of these difficulties and may enable simplification of measurements of flow velocity.

BRIEF SUMMARY OF THE INVENTION

According to the invention there is provided a Doppler flowmeter for measuring blood flow in a vascular channel, comprising: an assembly of electro-ultrasonic transducers arranged to direct ultrasonic radiation to a zone spaced from the assembly and to receive radiation reflected therefrom, the transducers being spaced apart and capable of providing first and second radiation beam paths from a transmitting transducer to a receiving transducer after reflection from said zone such that the resultants of the beam paths lie in substantially opposite directions, and processing means coupled with the transducer assembly for receiving signals indicative of the reflected radiation having means for monitoring the instantaneous frequency difference between reflections derived from radiation following said first and second paths and for providing an indication proportional to said instantaneous frequency difference, the transducer assembly being operable to project radiation to said zone positioned within the channel such that part of the first path forms an acute angle with the direction of blood flow and part of the second path between the transducer assembly and channel forms an obtuse angle with the direction of blood flow, whereby the radiation frequency is Doppler shifted during reflection to provide frequency difference signals spaced in frequency by a factor related to flow velocity in the channel.

In one advantageous form the processing means comprises a multiplicity of narrow band pass filter channels each coupled with the transducer assembly and of frequency incremented spacing for passing signals of respective predetermined Doppler shifted frequency to respective outputs and a recording device having a continuously moveable recording tape and a multiplicity of writing devices coupled one with each filter output and arranged to write side-by-side across the tape in ascending order of frequency on receipt of a predetermined signal level from their respective filter to display a combined bar pattern the outline of which is a time velocity function of the maximum flow velocity at said zone in the vascular channel.

The assembly of electro-ultrasonic transducers may comprise a plurality of transducers arranged to direct ultrasonic radiation to a zone spaced from the device and to receive radiation reflected therefrom, the transducers being spaced apart and capable of providing first and second radiation beam paths from a transmitting transducer to a receiving transducer after reflection from said zone such that the resultants of the beam paths lie in substantially opposite directions.

The assembly may comprise two pairs of transducers each pair being mutually spaced apart and arranged to define mutually angled beam paths which intersect at a respective location in said zone.

Alternatively the assembly may comprise three transducer crystals arranged in spaced side-by-side sequence to define mutually angled beam paths therefrom which paths all intersect at a common zone spaced from the device.

In a presently preferred form of assembly the two outermost crystals of the sequence serve as ultrasonic beam transmitters and the intermediate crystal as a receiver, but these crystal roles can be reversed. Also, it is preferred that the beam path of the intermediate crystal extends as the bisector of the angle between the beam paths of the outer crystals, but again this is not critical — indeed, the former beam path need not even lie in the plane defined by the latter beam paths although this is desirable for purposes of compactness.

BRIEF DESCRIPTION OF THE DRAWINGS

In order that the invention and its various other features may be understood more easily embodiments thereof will now be described, by way of example only, with reference to the drawings, wherein.

DETAILED DESCRIPTION OF PREFERRED EMBODIMENTS

In a conventional system for measuring blood velocity by means of ultrasound a single transmitter and single receiver have been employed. The transducer for this system contains two piezoelectric crystals (one for the transmitter and one for the receiver) which usually are mounted side-by-side with roughly parallel beams which in some systems have been brought to coincide at a predetermined distance from the transducer. The velocity information is here obtained by measuring the frequency difference between a carrier-frequency or fixed local oscillator frequency used to excite the transmitter crystal and the Doppler-shifted energy, backscattered from moving blood corpuscles to the receiver. If V is the velocity of the blood-corpuscles in the channel, $fc$ is the carrier or transmitter-frequency, $c$ is the velocity of ultrasound in body tissue, and $\epsilon$ is the angle between the flow direction and direction of the transmitter-receiver beam then the difference frequency $fd$ between the transmitter frequency and the Doppler shifted frequency is given by the equation:

$$fd = \frac{2fc}{C} V \cdot \cos \epsilon$$

This difference $fd$ will, as it can be seen in the equation, be seriously dependent on $\epsilon$ since $\epsilon$ will be near 90° i.e. at the very steep part of the cosine function, when employed for work on vessels which run roughly parallel to the body-surface.

In the system of the present invention there are two doppler shifted signals produced by respectively differently directed reflections, and it is the difference between these signals which is observed to provide an indication of the flow velocity.

It will be appreciated that each of the doppler-shifted signals is composed of a spectrum of different frequency components and that the difference between these signals will be represented by a similarly complex signal. However techniques for the handling of such signals to facilitate observation, suitably by visualisation, have already been described in British Patent Specification No. 1,308,451 and similar techniques are equally appropriate to practical use of the present invention.

Figure 1:
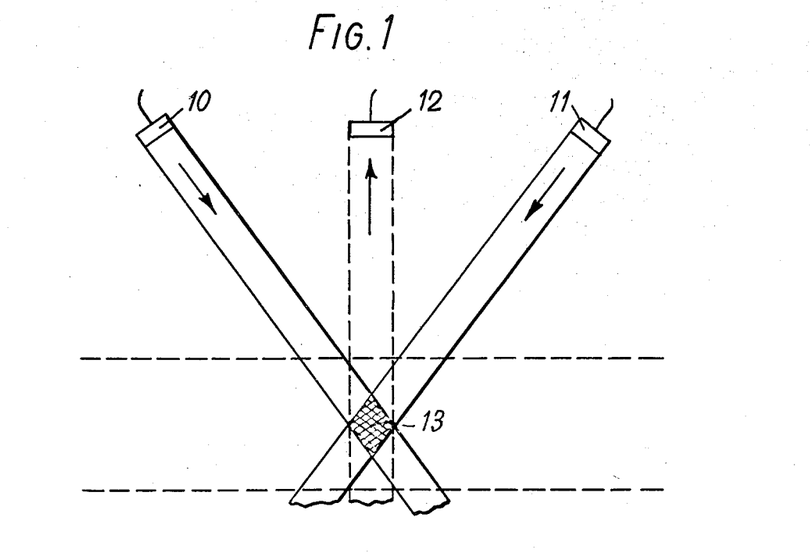
FIG. 1 shows schematically the beam paths of a basic transducer system employing three transducers and useable in a flowmeter in accordance with the invention.

One arrangement of the invention employs a three transducer structure as shown schematically in FIG. 1. The arrangement can be operated as shown using the transducers two as transmitters and one as a receiver, but alternatively two of the transducers could be used as receivers and one as a transmitter and still be within the scope of the invention. In FIG. 1 two transmitter-crystals 10 and 11 and one receiver-crystal 12 are mounted on a common plane. The two transmitter crystals 10 and 11 are directed such that when energized they generate two ultrasound beams which cross each other at a location spaced from the plane and form a scanning zone hereinafter termed the probe-volume 13. The receiver-crystal is arranged to receive scattered ultrasonic energy from this probe volume and can in principle be placed anywhere in relation to the two transmitter beams. For maximum sensitivity of reception however the transducer should be directed towards the probe volume so as to receive radiation directly along a beam path which intersects the probe volume.

Figure 2:
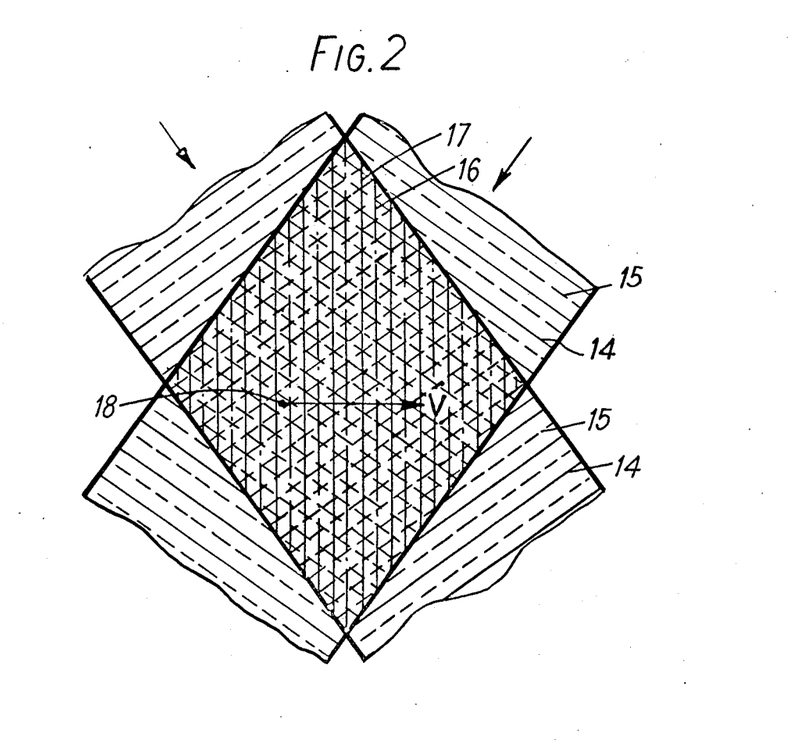
FIG. 2 shows an ultrasonic fringe pattern set up by the transducers of FIG. 1.

FIG. 2 shows an ultrasonic fringe-pattern which will be formed where the two transmitter-beams cross. The two transmitter beams comprise positive wavefronts 14 and negative wavefronts 15 and the fringe pattern is made up of nodes 16 and antinodes 17. When a particle (blood corpuscle) 18, is present in the fringe-pattern, ultrasonic energy will be scattered and radiated from the particle. The directional characteristic of the scattered radiation from the particle will depend upon its acoustic impedance, shape and size, but for blood-corpuscles, which are much smaller than the ultrasonic wavelength, the radiation will be more or less omnidirectional. This again means that the scattered energy will be present in all directions relative to the particle but with varying strength. When the particle, as in the blood-stream, is moving in the direction as shown in FIG. 2, it will pass through the fringe-pattern (nodes and anti-nodes) and the scattered energy will be amplitude-modulated with frequency according to the density of the fringe-pattern and according to the velocity of the particle. The density of the fringe-pattern is determined by the transmitter frequency and the angle between the two transmitter beams, and it is constant and known.

The fringe-pattern planes are parallel to the axis of the system which in the case illustrated are orthogonal to the transducer-plane or surface-plane (See FIG. 1). This means that the highest modulation frequency at the scattered ultrasound, will occur when the particle with the velocity V is moving parallel to the surface plane, as shown in FIG. 2. This is a favourable situation for obtaining velocity information for vessels which are roughly parallel to the body surface. That the modulation frequencies in the signal, received by the receiver transducer is approximately independent of where the receiver transducer is placed can most easily be understood when it is remembered (as shown) that the amplitude modulation of the particle in the fringe-pattern really occurs as a result of having several frequencies present very near the carrier-frequency. These frequencies seen at the receiver crystal, have been Doppler-shifted (dependent on the velocity of the particle and position of the receiver transducer) with nearly the same frequency displacement. The absolute distance between the frequencies which formed the modulation remains app. constant and the modulation frequencies will not be changed.

Figure 3:
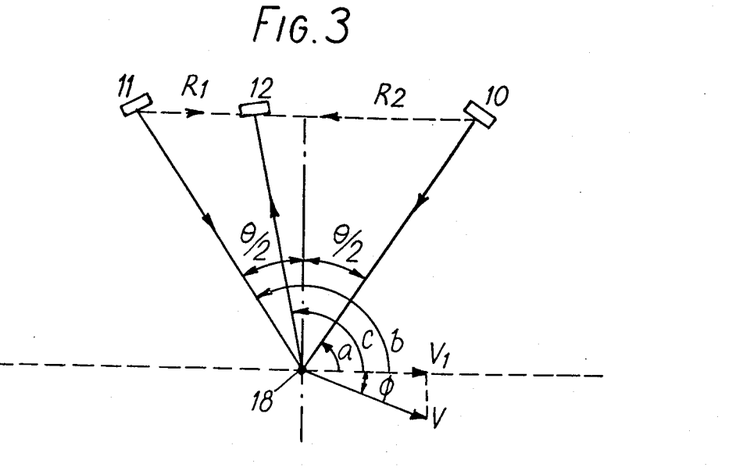
FIG. 3 is a beam array pattern produced by the transducer system of FIG. 1.

The beam array pattern is shown in FIG. 3 in use for measuring a flow velocity V inclined relative to the transducer plane. It will be seen that the radiation beam paths from the transmitters to the receiver have resultant directions R1 and R2 which lie in substantially opposite directions, in this case towards each other. When the particle, P, is moving with the velocity, V, through the cross-point it will begin to vibrate and radiate an ultrasound-signal containing two different frequencies, even if the frequencies in the two transmitter beams are the same. The reason is that the beam-frequencies are Doppler-shifted in two different directions before being radiated from the particle. It is the difference between the two Doppler-shifted frequencies which is of particular relevance and to a first approximation independent of the angle $\phi$ between the flow direction and the transducer plane.

The signal received at the receiver transducer may not contain the same two frequencies as those radiated by the particle. Since they might have been Doppler-shifted again. However, the distance between the two frequencies will to a first approximation remain constant. That the equation is independent of the receiver-position can also be seen by reference to the following calculations. The angles involved in the arrangement are clearly shown and require no further explanation. $fc$ is the frequency of the transmitted ultrasound, $\lambda$ is the wavelength of sound in tissue, and $c$ is the velocity of sound in tissue. $fpa$ and $fpb$ are the Doppler frequency shifted values radiated by transmitters 10 and 11 respectively and $fra$ and $frb$ are the frequency shifted values received by receiver 12 due to the transmission from 10 and 11 respectively. The equation for the system is derived mathematically as follows:

Frequency induced by transmitter 10

$$fpa = fc + \frac{V1 \cdot \cos a}{\lambda} \quad (1)$$

$$fra = fpa + \frac{V1 \cdot \cos c}{\lambda} \quad (2)$$

Frequency induced by transmitter 11

$$fpb = fc + \frac{V1 \cdot \cos b}{\lambda} \quad (3)$$

$$frb = fpb + \frac{V1 \cdot \cos c}{\lambda} \quad (4)$$

The wanted difference frequency: $fd = fra - frb = fpa - fpb$ $$fd = \frac{V1 \cdot \cos a}{\lambda} - \frac{V1 \cdot \cos b}{\lambda} = \frac{V1}{\lambda}(\cos a - \cos b)$$

$$fd = \frac{V1}{\lambda} \cdot 2 \sin \frac{a+b}{2} \cdot \sin \frac{b-a}{2} \quad (5)$$

From FIG. 3:

$$V1 = V \cos \phi \quad (6)$$

$$\theta = b - a \quad (7)$$

$$a + b = 180° \quad (8)$$

Eq. (6), (7) and (8) substituted in (5):

$$fd = \frac{2 \cdot V}{\lambda} \cos\psi \cdot \sin \theta/2 \quad (9)$$

or:

$$fd = \frac{2 \cdot V \cdot fc}{c} \cos\psi \cdot \sin \theta/2 \quad (10)$$

The derived equations are still an approximation as the fundamental Doppler-equations used are approximate and as $\lambda$ in eq. (2) and (4) should have been modified.

Equation 10 shows how the Doppler-frequency difference $fd$ is related to velocity V in the configuration of the cross-beam-system, we have been discussing.

In one form of transducer assembly, with fixed transducers, the angle $\theta$ will be constant, but can be calculated during design such that the range of $fd$ is a required value when all other variable are given $\phi$ which is the angle between the transducer plane or the body surface and the direction of the blood flow will for most vessels be near zero, where the cosine-function is fairly flat. $fd$ will be nearly independent of $\phi$ for most accessible blood vessels such as the limb-vessels, the carotid artery etc. In fact, providing $\phi$ is within $\pm 25°$ the resultant value of $fd$ will be measured to an accuracy within $\pm 10\%$.

In the stationary fringe field, shown in FIG. 2, it would not be possible to distinguish between the modulation caused by a particle moving in one direction and one moving in the opposite direction. Nevertheless, it is possible to change the stationary-pattern into a moving one, simply by feeding the two transmitter crystals with two slightly different frequencies $fc1$ and $fc2$. A stationary particle in the moving pattern will now scatter ultrasonic energy which is modulated with the frequency-difference between the two carriers, $fc1-fc2$. If the particle is moving in the same direction as the fringe-pattern, this difference frequency between the two carriers is reduced by $fd$ by Doppler effect as calculated in equation 10. If the particle-velocity goes in opposition direction to the pattern-velocity, the modulation frequency will be increased. A condition for this directional-resolving velocity-measuring system to work is that $fc1 - fc2 > fd$ max.

Figure 4:
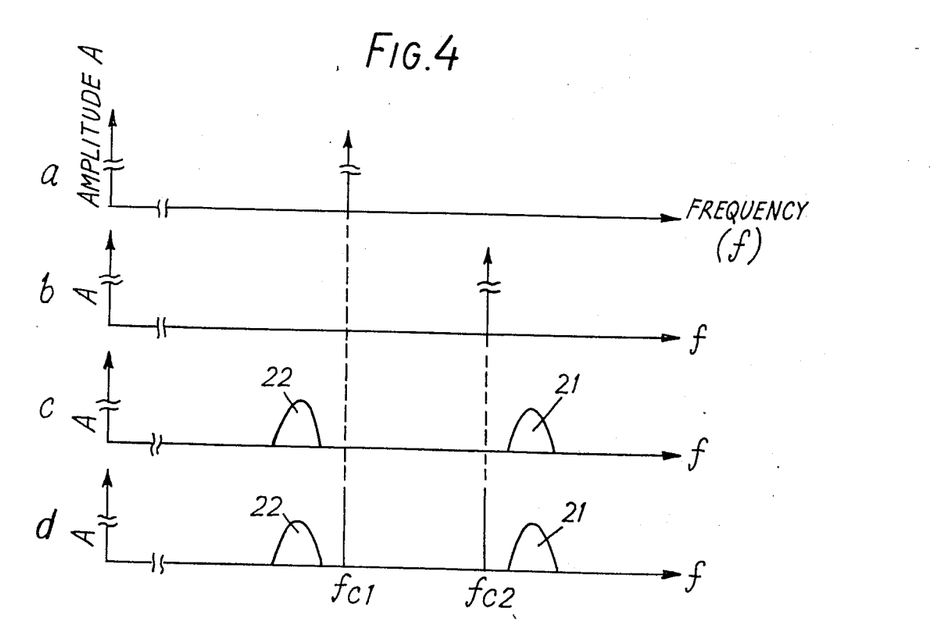
FIGS. 4a to 4d show amplitude/frequency diagrams relating to the system of FIGS. 1 and 3.

In order to analyse the directional resolving cross-beam system in closer detail and to discuss the difficulties in the system one graphical frequency-spectrum method will now be described with reference to FIG. 4.

In the system as shown in FIGS. 1 and 3, where the two transmitter beams have opposite inclination to the direction of flow, and where the receiver-transducer is placed symmetrically between the two receivers, a frequency-domain configuration as shown in FIGS. 4a to 4d will apply. The relative distribution of amplitude and frequency shown in FIG. 4 are only for illustrative purposes as the actual shape will depend upon flow-profile, probe-volume position and size, time course etc.

Figure 5:
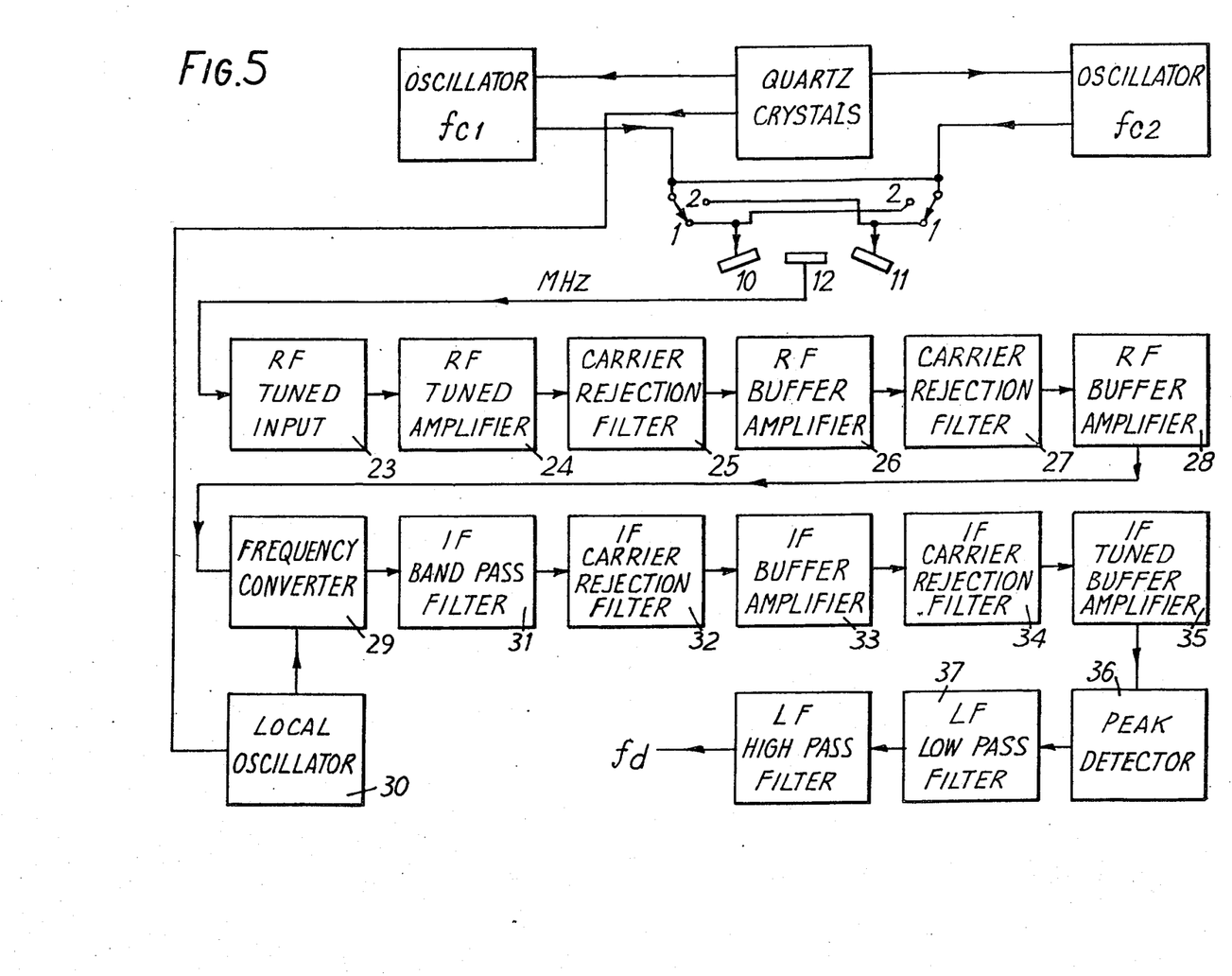
FIG. 5 is a block schematic diagram of one processing system forming part of a Doppler flowmeter arranged in accordance with the invention.
Figure 6:
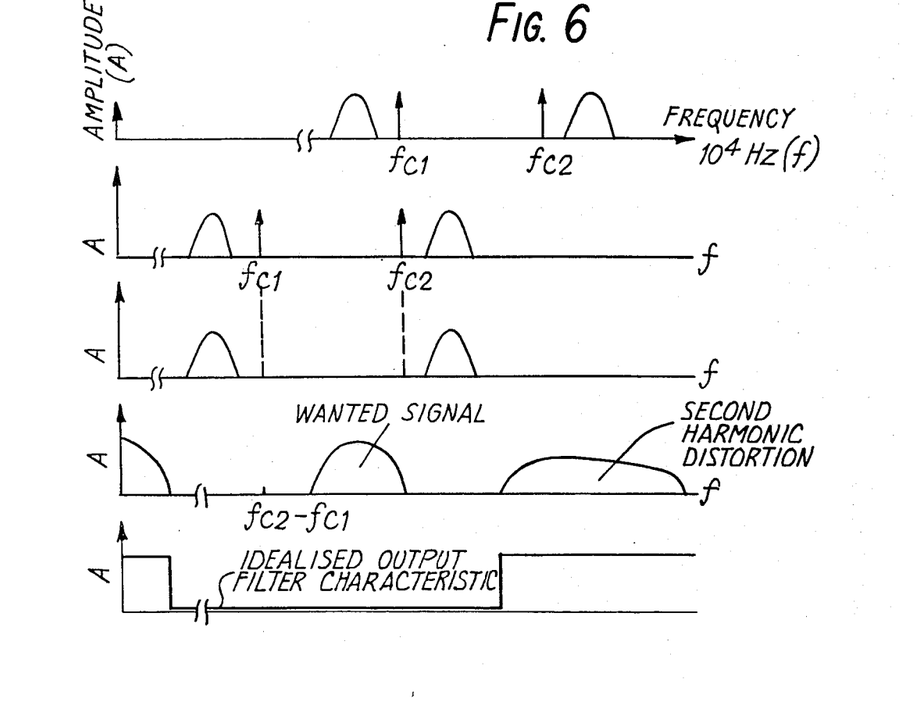
FIGS. 6a to 6e show amplitude/frequency diagrams illustrating sequentially the processing steps involved in the arrangement of FIG. 5 at different points along the processing path.

FIGS. 4a and b shows the frequencies of the transmitters 10 and 11 respectively with a frequency-difference, which is of the order of 10 kHz. FIG. 4c shows the signal obtained by the receiver-transducer in the idealised case where the receiver transducer is receiving signals only from the probe volume. Two received, Doppler-shifted spectra 21 and 22 will be placed higher and lower than the transmitted frequencies (as shown in FIG. 4c) when the blood-corpuscles are moving through the ultrasonic field pattern in the direction as shown in FIGS. 1 and 3, where the two transmitters have frequencies as shown in FIGS. 4a and b. If the flow is going in the opposite direction, the received spectra will be placed between the two transmitter-frequencies. FIG. 4d shows a practical case where two strong carrier-frequencies $fc1$ and $fc2$ are also present at the output of the receiver-transducer. This is partly caused by direct coupling between transmitter-transducers and receiver-transducer and partly by reflections from tissue interfaces which are stationary and are orientated in such a way that they can reflect energy from the transmitter-transducer to the receiver. These frequencies will not quite be a line in the frequency-spectrum, as shown in FIG. 5d, but will be broadened because of the Doppler-shift from slow interface-movements (vessel-wall-movements). As it will be shown, it is necessary to reject those "broadened carrier frequencies" before demodulation.

The wanted, angle-independent Doppler-information will be the difference between the two spectra 21 and 22 with no reference to any fixed frequency. The two spectra will move when the flow direction differs from being parallel to the transducer plane, but the frequency difference will, to a first approximation, remain constant. To obtain the difference-frequency-spectrum, some kind of non-linear processing can be effected (i.e. square-law-detection or peak-detection) and a strong fixed carrier if present during the processing would make the system angle-dependent as the distance between the carriers and the wanted "floating" spectra 21 and 22 would not be constant with angle.

FIG. 5 shows one possible processing system and FIGS. 6a to 6e show the steps in the processing as they are carried out along the processing path. The two transmitter transducers 10 and 11 are excited from respective crystal controlled oscillators at frequencies $fc1$ and $fc2$. The receiver 12 receives the reflected signal which comprises Doppler shifted frequencies and the transmitter frequencies.

The received signal is passed through an input circuit tuned to accept the radiation, which may be in the range of 2–16 MHz, and then through a tuned R.F. amplifier 24. The two carriers are then attenuated in two notch-rejection-filters 25 and 27, which are quartz crystal filters which reject $fc1$ and $fc2$ respectively and which are coupled via a buffer amplifier 26. Then the signals are passed via another buffer amplifier to a frequency converter 29 where they are converted in frequency from the working frequency (MHz-region) to an IF-region which is in the tens of kHz-region by beating with a local oscillator 30. The transformed carrier frequencies are now approximately 100 times lower, and it is much easier to construct a bridge-filter with a sufficiently narrow bandwidth (in absolute frequency terms) to reject the residual components of the two carriers. The output signal from the frequency converter 29 is passed through a band pass filter 31 tuned to the IF frequency and two IF carrier rejection filter bridges 32 and 34 which reject respective ones of the transformed carrier frequencies. The filter bridges are coupled via a buffer amplifier 33. The output from filter bridge 34 is passed via an IF tuned buffer amplifier 35 to a peak detector 36. The two wanted velocity-spectra are shown in FIG. 4c. The signal is now non-linearly processed in the detector 36 and after having filtered the wanted spectrum out of the signal, by means of LF low pass filter 37 and LF high pass filter 38, we are left with a signal $fd$ which contains the angle-independent velocity-information. This information can now be processed in various ways as hereinafter described. The system can, in principle, be divided into three parts:

1. The Transducer: which by its special transmitter-receiver-configuration obtains a signal which contains the wanted signal-information as well as unwanted signals.
2. The Electrical Pre-processing System, which amplifies the signal and picks out the wanted velocity information.
3. The Final Signal-processing and Display System: where existing methods can be used to translate the wanted velocity information into a visual or stored form indicative of the flow velocity.

1. The Transducer

In the specifically described arrangement this differs from known transducers. It has a special three-point geometry and here again although the configuration is described with two transmitter-crystals and one receiver crystal a system is equally possible with the reverse arrangement. The transducer principle has already been shown in FIGS. 1 and 3. The transducer can be constructed in various different ways, dependent on for which purpose and which flexibility of use is required.

a. The three crystals can have fixed positions and angle in relation to each other.
b. The distance between the transmitter-crystals can be made adjustable without altering their relative inclinations and by that means the depth-range can be adjusted.
c. Different angles, $\theta$ can be used to give different frequency ranges for the Doppler signal (must be seen in relation to the ultrasonic vibration-carrier-frequency).
d. Combinations between $a$, $b$ and $c$ can be used.
e. The transducer can be made as a surface-transducer for transcutaneous purposes.
f. The transducer can also be mounted on a catheter for invasive purposes.
g. A transducer can be formed with two pairs of crystals each pair being arranged with one as a transmitter and one as a receiver as hereinafter described.

Figure 7:
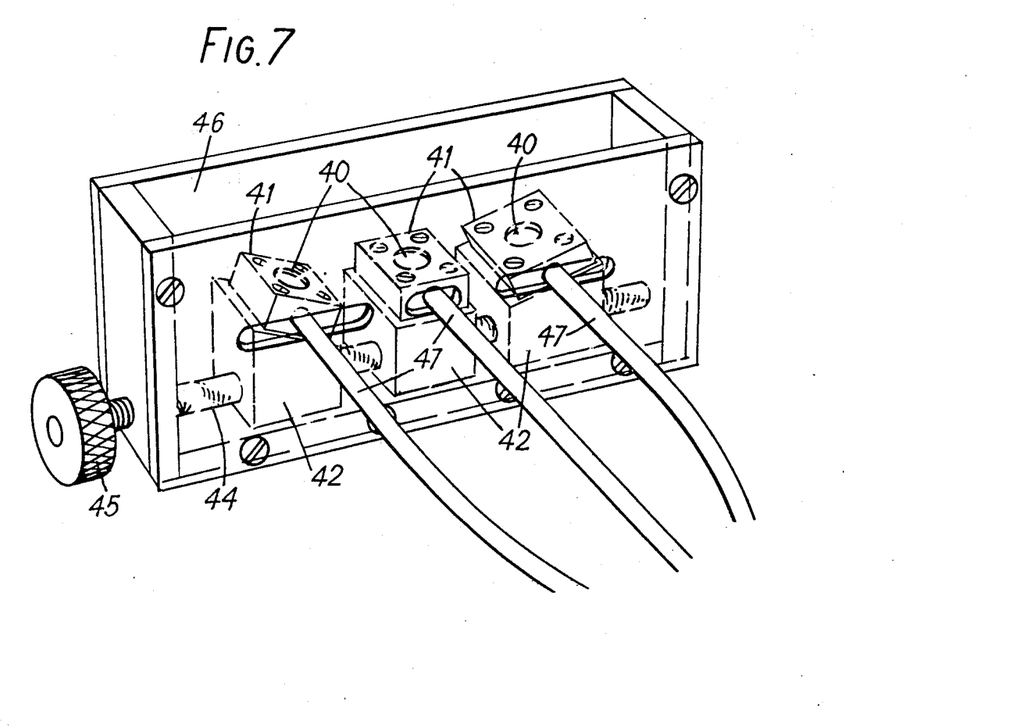
FIG. 7 is an isometric view of a transducer assembly having three transducers and means for adjusting the depth scanned and useable in a flowmeter in accordance with the invention.
Figure 8:
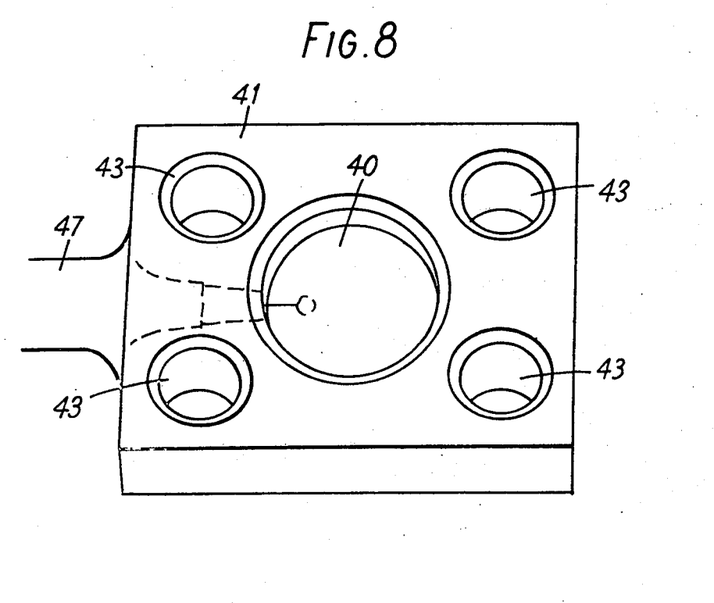
FIG. 8 shows in greater detail a single transducer block as used in the assembly of FIG. 7 and FIGS. 9 and 10.

A transducer assembly having adjustable depth range is shown in FIG. 7. The transducer block is shown in FIG. 8. The assemblies are each mounted in a perspex housing. Three transducer discs 40 (5 mm in diameter, 6 MHz, PZT5 - ceramics) are mounted in a housing in three similar small perspex blocks 41 (as shown in FIG. 8) in such a way that the crystal is held at its periphery transversely of a central aperture and is air-backed over 90% of the crystal area. The three perspex blocks are mounted on one fixed and two adjustable brass-blocks 42 by screws passing through holes 43. The angle of the two adjustable blocks is designed according to equation (10). A left-hand and right-hand thread on a common adjustment shaft 44 moves the two wedge-shaped brass blocks towards each other or away from each other when a finger wheel 45 is rotated and this adjusts the depth at which the beams will intersect. The contact between the transducer-crystal and the skin surface is obtained by means of ultrasonic contact jelly contained in the housing between the transducers and an open side 46. The transducers can be linked to associated exciting signals or to respective processing equipment via screened transmission leads 47. With the angle between the transmitter beams as shown in FIG. 3, $fd$ is 3 kHz when the velocity parallel to the transducer plane is 100 cm/sec.

Figure 9:
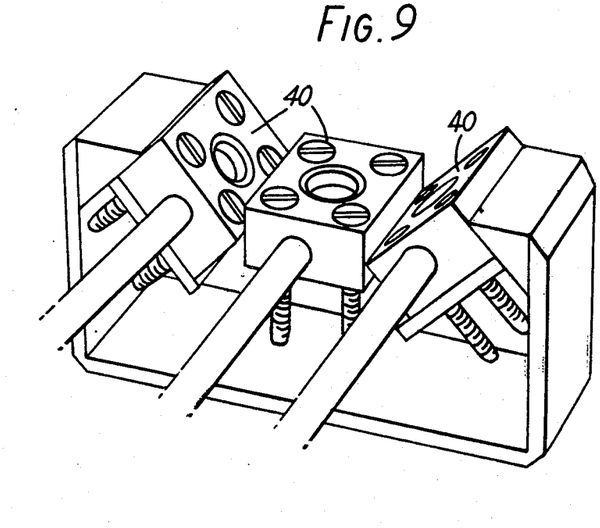
FIG. 9 shows an isometric view of a transducer assembly in accordance with the invention.
Figure 10:
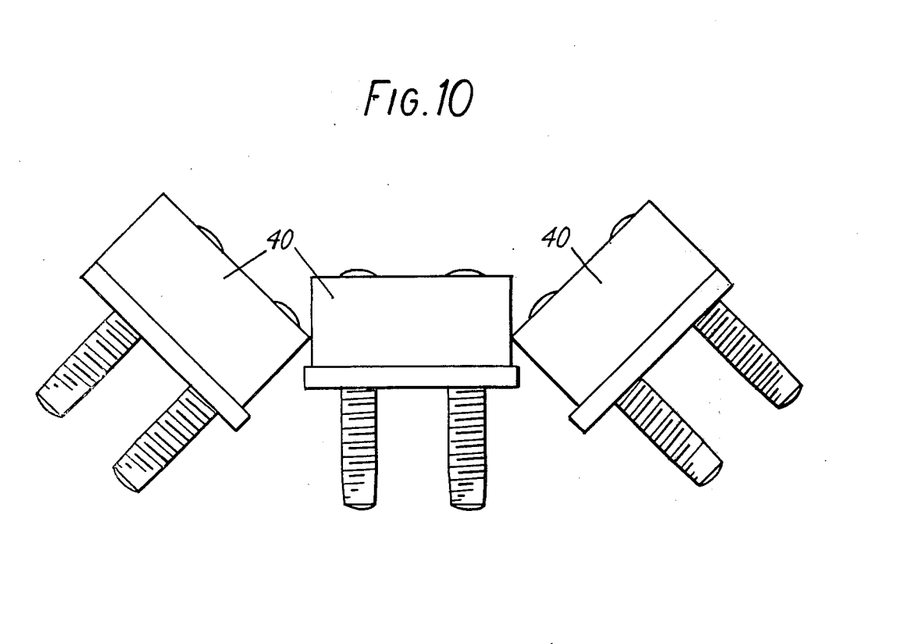
FIG. 10 is a side view of the assembly of FIG. 9.

FIGS. 9 and 10 show a transducer assembly with three transducer blocks 40 mounted in a fixed disposition. As can be seen $\theta = 90°$. The depth-range is fixed and centred approximately 1 cm from the transducer plane. By using $\theta = 90°$, $fd = \pm 3$ kHz will be caused by the velocity ± 54 cm/sec. The crystals are in contact with the skin by means of ultrasonic jelly.

2. The Electrical Pre-processing System

This system is needed for providing the transmitter-crystals with the needed R.F. power. The two transmitters 10 and 11 are quartz-crystal-controlled and operate at frequencies $fc1$ and $fc2$ (in the 2–16 MHz region and of the order of 10 kHz apart, $fc1 - fc2 > fd$ max). The signals from the receiver-transducer will be amplified and the unwanted carrier frequencies $fc1$ and $fc2$ will be rejected in this electronic unit. Furthermore, the wanted angle-independent Doppler signal will be formed in the detector of the pre-processing unit. The various output filters are included to ensure that unwanted harmonic distortion is not present at the output. It will be seen that the carriers are rejected in two steps. First, the two carriers are attenuated in input-filters 25 and 27 (quartz-crystal filter). This gives a predetermined rejection and does ensure that the R.F. amplifier and frequency-converter will not be overloaded. The second rejection filters 32 and 34 are placed after a frequency conversion has taken place. These filters can be made very narrow in terms of frequency selection, as their centre-frequency now is low in relation to the transmitter frequency. In dependence on the amount of carrier in the received signal (which will depend on the application of the system) it may be possible for one of the rejection filters to be left out. The band pass-filter after the frequency-converter ensures that any prematurely demodulated signals (caused by non-linearities in previous stages) cannot pass through to the demodulator. The demodulator is here shown as a peak-detector but could also be for example a square-law-detector. The purpose is to form the difference frequency as explained in graphical part. To reduce temperature drift the two transmitter-crystals and the local oscillator crystal can be mounted in the same box.

The pre-processor can be built according to the system described with reference to FIG. 5, although the two R.F. notch-crystal filters can be left out and the carriers rejected in the two filters after the frequency-converter. The two transmitter frequencies can be for example 6,000,000 Hz and 6,008,100 Hz which gives an off-set-frequency of 8.1 kHz.

3. The Final Signal-processing and Display-system

The output signal from the pre-processor is an L.F. signal where zero flow velocity will have the frequency $fc1 - fc2$ (this frequency will, in fact, not be present if the rejection filters are ideal). The Doppler-frequencies will be higher or lower than the frequency $fc1 - fc2$, dependent of the directions of the flow in the blood stream.

The final processing can be carried out in various already known ways e.g.

a. Zero-crossing technique.
b. Frequency-tracking-technique (phase locked loops).
c. Spectrum analysis (i.e. parallel filter-bank).

In practice, to obtain a proper signal from the transducer it is desirable to avoid formation of air-bubbles in the jelly where the ultrasonic beams are passing. Even small air-bubbles can easily reflect energy to the receiver-transducer and the carrier rejection in the preprocessor may not in such circumstances be sufficient. In this respect the adjustable transducer of FIG. 7 is more prone to air bubbles introduced to the jelly.

Figure 11:
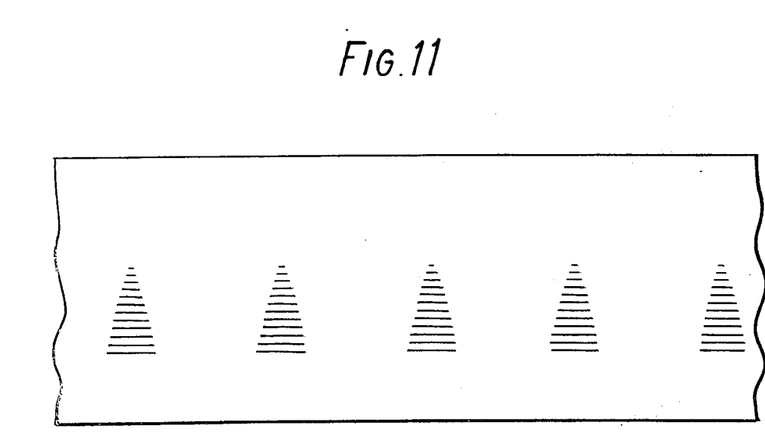
FIG. 11 graphically illustrates a bar frequency display plotted on a time scale as produced by a suitable output transducer device.
Figure 12A:
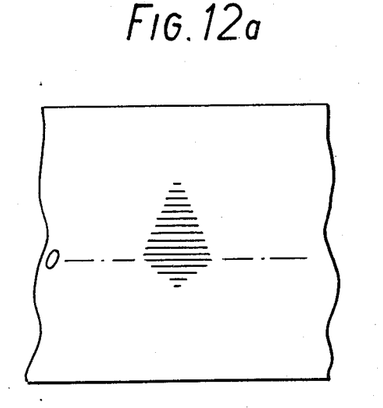
FIGS. 12a and b show graphical illustrations of bar frequency displays plotted on a time scale produced again by a suitable output transducer device and enabling flow direction to be distinguished.
Figure 12B:
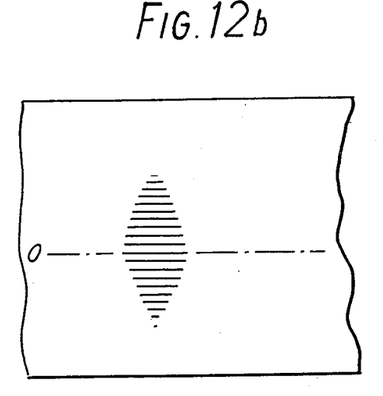

The transducer shown in FIGS. 9 and 10 has given very promising results. It has not been possible to measure any change of importance in peak velocity when the transducer is tilted approximately ±15°. The sort of display one gets when the T.A.V. equipment used as spectrum analyser and with an output transducer device as described in British Patent No. 1,308,451 for providing a visual display is shown in FIG. 11 on a continuously movable recording ribbon. The picture shows the forward velocity of a brachial artery in the above position. Each bar is representative of a particular frequency component of the processed signal and the envelope produced by the bar pattern defines a plot of maximum Doppler shifted frequency plotted against time which is a function of flow velocity. The diagram of FIG. 11 represents frequency shift independent of flow direction. In order to distinguish between flow directions it is desirable to display separately the doppler shifted frequencies of each of the basic transformed transmitter frequencies as received by each receiver in side by side disposition as shown in FIGS. 12a and 12b. The frequency will go from 5 kHz to 11 kHz when the velocity goes from − 100 cm/sec to + 100 cm/sec for the adjustable system and from − 54 cm/sec to + 54 cm/sec for the fixed system. This system is designed to suit the spectrum analyser and writer-part of the instrument for transcutaneous aortovelography (T.A.V.) developed by Henry Light and Geoff Cross, Bioengineering Division, Clinical Research Centre. The spectrum analyser of this instrument is able to handle the frequency-band from 5 kHz to 8 kHz, so flow in one direction only can be displayed at any one time. In the block-diagram, FIG. 5, switch means is shown by which the two transmitter beams can be interchanged, which means that flow in both directions can be analysed. The preprocessor instrument can have two knobs for adjusting independently the two transmitter drive levels, and one R.F. and one I.F. gain-control can be provided in the receiver part.

It may not be necessary to include any adjustment means for some applications or alternatively the number of such controls may be reduced.

The zero line shown in FIG. 12a represents zero frequency displacement, i.e. no flow existing in the channel. The bars above the line represent increased frequency components due to the Doppler effect and those below the line represent reduced frequency components due to the Doppler effect. As can be seen, the envelope is non-symmetrical relative to the zero line. In dependence on whether the waveform is predominately on one side or the other of the zero line is an indication of direction of flow. The maximum velocity of corpuscular flow is measured by scaling the peak height of the envelope measured transversely of the tape but measurements at different time instants can be made to obtain values of for example of the mean flow velocity. The scaling of the bars gives a measure of the difference between the Doppler shifted frequencies at a particular instant in time and as can be seen from the equation 10 this is directly proportional to the flow velocity when angles $\phi$ and $\theta$ are maintained constant. The tape can therefore be scaled transversely directly in velocity and can be provided with scale lines extending longitudinally along its length.

An alternative method of determining flow velocity and also to obtain maximum sensitivity is to adjust the inclination of the transducer assembly such that the envelope is symmetrical about a common null axis as shown in FIG. 12b. Attainment of the requisite symmetry may be effected simply by the use of a semisilvered mirror along the null axis plane of the display.

Direction information can be alternatively provided by employing equipment which is capable of resolving the flow direction appropriate to one Doppler-shifted signal and occasionally switching off one of the beams in a double transmission device. When symmetry occurs then the central beam is normal to the flow direction and the velocity of flow is proportional to twice the envelope height measured perpendicularly to one side of the centre line. Again the tape could be suitably scaled to provide a direct read out.

Instead of providing the graphical display it will be appreciated that the difference signals could be processed electronically and could be recorded or displayed directly in velocity and direction of flow.

Other system-configurations of transducer as well as signal processing than the one discussed can be employed.

Figure 13:
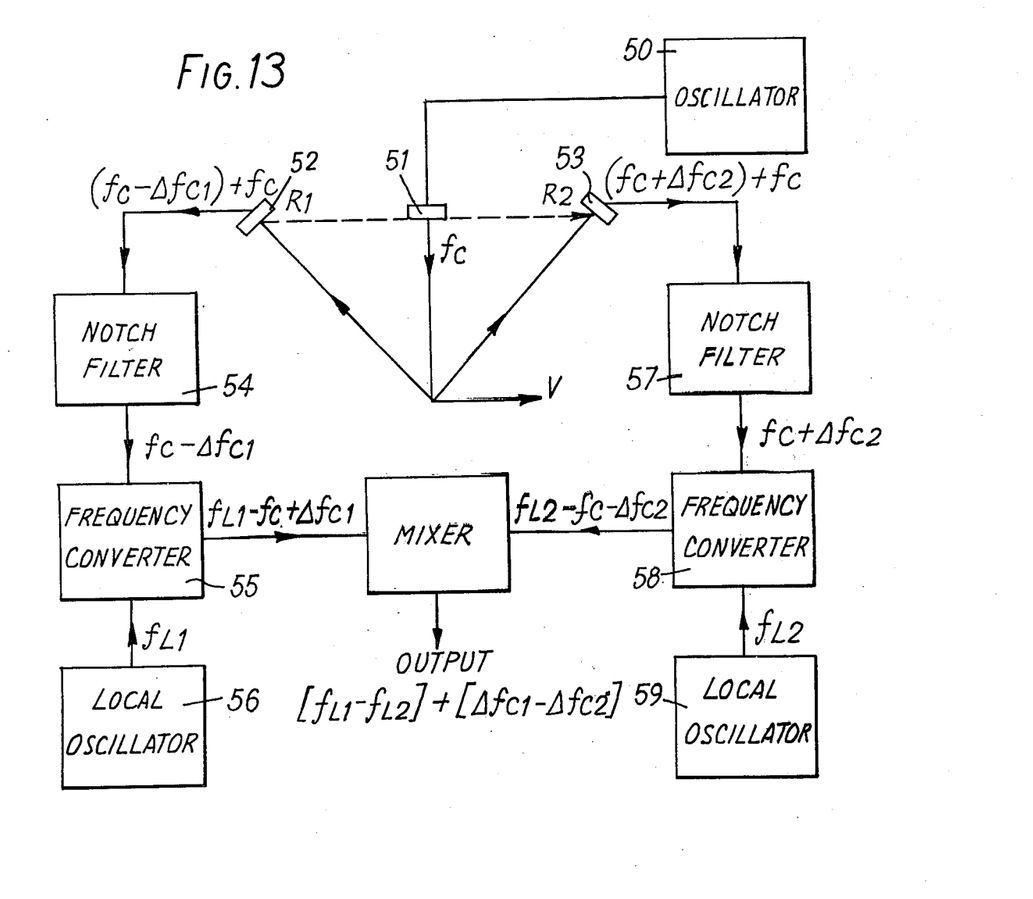
FIG. 13 is a block schematic diagram of an alternative system employing a three transducer assembly such as the transducer systems of FIGS. 7 or 9.

FIG. 13 shows a system employing the transducer assemblies of FIGS. 7 or 9 but this time with one transmitter transducer and two receiver-transducers. This system also has directional-resolving capabilities. As the two receiver signals have to be mixed or multiplied, it is also here necessary to reject the carrier before this process takes place.

Figure 14:
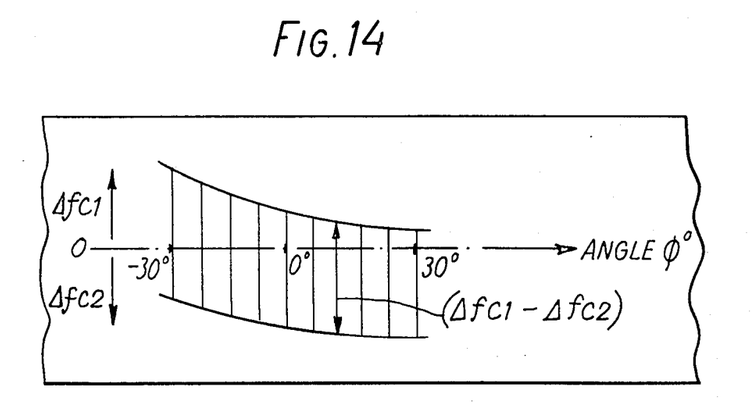
FIG. 14 illustrates a spectrum analyser display in which two doppler shifted frequencies are displayed separately.

The main difficulty in the discussed systems is if a strong carrier or carriers present in the non-linear process. One way of getting around this problem is to do the final processing (i.e. spectrum-analysis) at both signals I and II and subtracts the two output answers from each other. There would be no non-linear processing and no filtering would be needed, but the final processing would be much more troublesome (the spectrum-analysis-representation is not a simple voltage versus time, but often a parallel representation. In such an arrangement a separate display of $\Delta fc1$ and $\Delta fc2$ is employed as shown in FIG. 14. The angle-independent dimension is the distance between their representations.

In this arrangement a single transmitter frequency is generated by an oscillator 50 which is coupled to to the intermediate transducer which here operates as a transmitter 51 to direct the ultrasonic radiation into the channel. The radiation is modulated by movement of corpuscles in the channel and produces, by Doppler effect, difference frequencies which are picked up by receiver transducers 52 and 53. As can be seen the resultants R1 and R2 of the beam paths from the transmitter to the receivers, shown dotted, again lie in substantially opposite directions. The Doppler shifted frequency received by receiver 52 is $fc - \Delta fc1$, where $fc$ is the oscillator frequency. This frequency is combined with a frequency component at the oscillator frequency. The oscillator frequency is substantially attenuated in a notch filter 54 and the filtered frequency components are transformed to a lower frequency in a frequency converter 55 by mixing with a signal derived from a local oscillator 56 of frequency $F_{L1}$. The major component of the resultant signal is $fL1 - fc + \Delta fc1$. A similar procedure is involved in transforming the signal output from the receiver transducer 53 which contains a Doppler shifted frequency component $\Delta fc2$ as well as a component $fc$. The transformation is via notch filter 57, arranged to substantially attenuate $fc1$ and frequency converter 58 which mixes the signal with a frequency $fL2$ derived from local oscillator 59. The output from converter 58 contains the major frequency components $fL2 - fc - \Delta fc2$. The output signals from the two converters 55 and 58 are mixed in a mixer 60 to provide an output signal $(fL1-fL2) + (\Delta fc1 + \Delta fc2)$. The first of these frequency components represents an offset frequency introduced by the two local oscillators 56 and 59, whilst the latter represents the wanted signal which is related to the velocity V of flow in the channel. This signal can be processed by a final signal-processing and display system as hereinbefore described.

Figure 15:
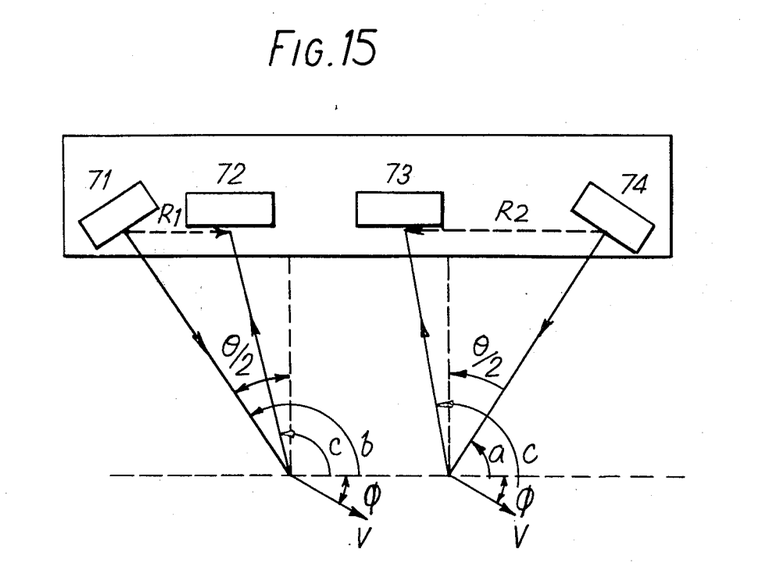
FIG. 15 is a side view of a transducer system employing four transducers and useable in a flowmeter in accordance with the invention.

A transducer employing four transducers is illustrated in FIG. 15. The transducers are arranged in pairs 71, 72 and 73, 74. The pairs are suitable for operation one as a transducer and the other as a receiver. In the beam array pattern of FIG. 15 such a four transducer assembly is shown in which the outer transducers 71 and 74 act as transmitters and the inner transducers act as receivers. The angles shown correspond with those shown for FIG. 3 and the Doppler equation 10 already derived similarly applies to this system. It will be appreciated however that a four transducer system in which the angles between the transmitted or received beams in each pair differ i.e. are not both equal to $\theta/2$. Such an arrangement modifies the basic equation 10 but still enables the advantages of the invention to be obtained. As can be seen the resultants of the beam paths from transmitter to receiver lie in substantially opposite directions. It will be appreciated that transducers 72 and 73 could be employed as transmitters and transducers 71 and 74 as receivers. The processing of the signals derived from the receivers can be effected in the same manner as has been described for the three transducer system.

In FIGS. 1, 3, 13 and 15 all crystals are mounted in the same plane. This is not essential and as earlier mentioned, the common crystal of the three transducer assembly (the middle one) could be mounted in a different plane provided it is aimed generally towards the cross-point of the two symmetrical placed transducers. Nevertheless the shown configurations are preferable for transcutaneous work in that access is then only required from one side.

Experience in transcutaneous work, shows that the transducer crystals preferably should be close to the skin, so that only a thin layer of jelly is needed. The fixed depth range transducer of FIG. 9 is particularly convenient, as it can be made small and handy. To enable different depth vessels to be monitored it is preferred that a set of several transducers with different fixed depth-ranges be provided. The R.F. notch-filter is not easily dispensed with as a strong carrier frequency can easily cause overloading of the amplifier-stages.

The new principle for angle-independent blood-velocity measurement which has been described is particularly suitable for use with apparatus for transcutaneous aortovelography. The new instrument will be useful at work on superficial vessels which run roughly parallel to the body-surface, but also catheter versions are possible. It is of special value in the study of changes in blood flow to the limbs and to the brain.

What we claim is:

1. A Doppler flowmeter for measuring blood flow in a vascular channel, comprising: an assembly of electro-ultrasonic transducers arranged to direct ultrasonic radiation to a zone spaced from the assembly and to receive radiation reflected therefrom, the transducers being spaced apart and capable of providing first and second radiation beam paths from a transmitting transducer to a receiving transducer after reflection from said zone such that the resultants of the beam paths lie in substantially opposite directions, and processing means coupled with the transducer assembly for receiving signals indicative of the reflected radiation having means for monitoring the instantaneous frequency difference between reflections derived from radiation following said first and second paths and for providing an indication proportional to said instantaneous frequency difference, the transducer assembly being operable to project radiation to said zone positioned within the channel such that part of the first path forms an acute angle with the direction of blood flow and part of the second path between the transducer assembly and channel forms an obtuse angle with the direction of blood flow, whereby the radiation frequency is Doppler shifted during reflection to provide frequency difference signals spaced in frequency by a factor related directly to flow velocity in the channel.

2. A flowmeter as claimed in claim 1, wherein the processing means comprises a spectrum analyser coupled with the transducer assembly for providing a visual display of the Doppler shifted spectrum and scaled to enable measurement of maximum frequency spacing between radiation components derived from first and second paths.

3. A flowmeter as claimed in claim 1, wherein the processing means comprises a multiplicity of narrow band pass filter channels each coupled with the transducer assembly and of frequency incremented spacing for passing signals of respective predetermined Doppler shifted frequency to respective outputs and a recording device having a continuously moveable recording tape and a multiplicity of writing devices coupled one with each filter output and arranged to write side by side across the tape in ascending order of frequency on receipt of a predetermined signal level from their respective filter to display a combined bar pattern the outline of which is a time/velocity function of the maximum flow velocity at said zone in the vascular channel.

4. A flowmeter as claimed in claim 3, wherein said writing devices are mounted in spaced apart disposition relative to a tape transport path of the recording device and wherein the tape width is subdivided by calibration lines extending longitudinally of the tape and defining the position of each writing implement each line being indicative of a predetermined Doppler frequency shift whereby maximum flow velocity at any recorded instant in time is determinable by the line spacing of the outline of the recorded bar pattern measured transversely of the tape.

5. A flowmeter as claimed in claim 1 wherein the processing means comprises a variable frequency oscillator coupled with the means for monitoring the frequency difference and phase lockable to the difference frequency between radiation derived from first and second paths, whereby the instantaneous oscillator frequency is proportional to flow velocity in said vascular channel.

6. A flowmeter as claimed in claim 1 wherein the processing means comprises a series arrangement of a frequency transposing means followed by a rejection means, said series arrangement being coupled between said transducer assembly and said means for monitoring the instantaneous frequency difference between reflections whereby the received radiation is shifted to a lower frequency band and frequencies outside a predetermined doppler frequency shifted range are attenuated.

7. A flowmeter as claimed in claim 1 wherein the assembly of electro-ultrasonic transducers comprises a device having a face adapted for location on the body of a patient, and two pairs of transducers located on said device each pair being mutually spaced apart and adapted to direct mutually angled beam paths which intersect at a respective location in said zone, whereby each pair directs transcutaneously respective separate beams one following a path having a portion forming an acute angle to the flow direction in a vascular channel and the other beam following a path having a portion forming an obtuse angle with the flow direction.

8. A flowmeter as claimed in claim 7 wherein the mutually outer ones of the transducers of the two pairs are coupled with an exciting source input, whereby they act as transmitters to direct a radiation beam at an acute angle and an obtuse angle to the flow direction in a vascular channel respectively and the inner one of each pair are coupled with the processing means, whereby they receive the radiation from their respective transmitter after Doppler shifted reflection from the channel and relay the received radiation to the processing means.

9. A flowmeter as claimed in claim 7 wherein the mutually inner ones of the transducers of the two pairs are coupled with an exciting source input, whereby they act as transmitters to direct respective radiation beams to the vascular channel and the outer ones of each pair are coupled with the processing means, whereby they receive the radiation from their respective transmitter along paths extending at an acute angle and an obtuse angle to the flow direction in the channel respectively and relay the received radiation to the processing means.

10. A flowmeter as claimed in claim 1 wherein the assembly of electro-ultrasonic transducers comprises a device having three transducers mounted thereon in spaced sequence to define mutually angled beam paths which intersect at a common zone spaced from the device.

11. A flowmeter as claimed in claim 10, wherein two of said three transducers are mounted such that their beam paths will intersect at substantially 90° and the other of said transducers will provide a beam path forming an acute angle with the beams of each of the other two transducers.

12. A flowmeter as claimed in claim 10, including adjusting means coupled with two of said three transducers and adapted to alter the disposition of the two transducers, whereby adjustment of said adjusting means influences the spacing from the device of said common zone at which zone the three beams intersect.

13. A flowmeter as claimed in claim 12 wherein the adjusting means is coupled with the outer ones of said three transducers and is adapted to move said two outer transducers relative towards or away from each other whereby adjustment of the spacing of said common zone from the device is effected without altering the relative beam angles.

14. A flowmeter as claimed in claim 10 wherein the outer ones of said three transducers are coupled with an exciting source input whereby they act as transmitters to direct a radiation beam at an acute angle and an obtuse angle to the flow direction in a vascular channel respectively and the intermediate one of said three transducers is coupled with the processing means, whereby the intermediate one of said three transducers is arranged to receive Doppler frequency shifted radiation derived from each transmitted radiation beam after reflection from the channel and to relay the received radiation to the processing means.

15. A flowmeter as claimed in claim 14 wherein the first and second exciting source inputs are coupled with respective ones of said two outer transducers which inputs are for different exciting frequencies, whereby ultrasonic radiation transmitted by the two outer transducers is of different frequency and the frequency difference between received Doppler shifted radiations is influenced by flow direction in the vascular channel.

16. A flowmeter as claimed in claim 10, wherein the inner one of said three transducers is coupled with an exciting source input, whereby it acts as a transmitter to direct a radiation beam into the vascular channel and the outer ones of said three transducers are coupled with the processing means, whereby the outer ones of said three transducers are arranged to receive said radiation, along paths extending at an acute angle and an obtuse angle to the flow direction in the channel respectively, after reflection from and Doppler frequency shifting in the channel and to relay the radiation to the processing means.

17. A flowmeter as claimed in claim 10 including frequency transforming means coupled with one of the outer transducers effective to introduced a predetermined component of frequency displacement between the signals received by the outer ones of the three transducers whereby said frequency difference monitored by said means for monitoring the instantaneous frequency difference is influenced by flow direction in the vascular channel.

* * * * *